United States Patent [19]

Di Florio

[11] Patent Number: Plant 6,133

[45] Date of Patent: Mar. 22, 1988

[54] *RAPHIOLEPIS INDICA* CV NEWPORT

[75] Inventor: Albert R. Di Florio, Irvine, Calif.

[73] Assignee: Weyerhaeuser Company, Tacoma, Wash.

[21] Appl. No.: 771,931

[22] Filed: Sep. 3, 1985

[51] Int. Cl.[4] ..... A01H 5/00

[52] U.S. Cl. ..... Plt./54

[58] Field of Search ..... Plt./54

*Primary Examiner*—Robert E. Bagwill

[57] ABSTRACT

A new and distinct variety of *Raphiolepis indica* which originated as a mutation in a group of cuttings taken from a parent "Jack Evans" variety. The new cultivar is particularly notable for flowers having a rich, vivid red-purple color, darker than any other known variety of *Raphiolepis indica*. The plant is of slow growing nature and tight, compact habit. Overall height of a fully mature plant is expected to fall in the range of 60 to 90 cm.

4 Drawing Figures

SUMMARY OF THE INVENTION

The present invention relates to a new and distinct plant cultivar of *Raphiolepis indica* ( L.) Lindl. shrub commonly known as "Indian Hawthorn" in the Rosaceae family.

This new Raphiolepis selection was discoverd during the spring of 1982 as a mutation originating from a population of asexually produced *Raphiolepis indica* 'Jack Evans' plants at Hines wholesale Nursery, 12621 Jeffrey Road, Santa Ana, Calif. 92705. This plant was selected and isolated as a distinct form for further evaluation. This new Raphiolepis selection has been reproduced numerous times by asexual propagation (vegetative cuttings). Each of the progeny exhibits identical characteristics to the original mother plant, establishing this selection as reproducible and true to type. Propagation is therefore retricted to asexual reproduction as any other means may disinherit the original characteristics.

This new Raphiolepis selection has many desirable and distinctive characteristics which render it unique from any other potentially similar *Raphiolepis indica* cultivar.

The unique, rich, vivid red-purple color of the flower petals (FIG. 1) is darker than any *Raphiolepis indica* cultivar that has ever been offered in the nursery trade (FIG. 2). Other distinct characteristics of this new Raphiolepis selection include its tight, compact habit (FIG. 3), slow growing nature and flower petals that remain cupped (never fully expanding; FIG. 4).

BRIEF DESCRIPTION OF THE PHOTOGRAPHS

The accompanying photographs show the unique rich, vivid red-purple color of the flower petals which is darker than any other *Raphiolepis indica* cultivar that has ever been offered in the nursery trade. Other distinct characteristics that are shown include the tight compact habit of the variety and flower petals that remain cupped, never fully expanding.

FIG. 1 is a close-up view of flowers of the new Raphiolepis cultivar demonstrating the rich, vivid red-purple color of the flowers.

FIG. 2 is a comparison of the new cultivar, at the center of the photograph, with the five other cultivars most similar to the present plant. Reading from left to right these are "Harbinger of Spring"; "Ballerina (produced at Bordier's Nursery); Ballerina (produced at Hines Nursery, Santa Ana, Calif.; Jack Evans, the parent plant of the new variety; and Coates Crimson.

DETAILED PLANT DESCRIPTION

After an extensive evaluation period, this new Raphiolepis selection was found distinct from any other Raphiolepis cultivar that is presently offered or has been offered in the past in the nursery trade. The following is a detailed description of this new *Raphiolepis indica* selection. Descriptions are based on not less than 20 specimens for each specified characteristic. Color determinations and comparisons are all based on The Royal Horticultural Society Colour Chart.

OVERALL SIZE AND GROWTH HABIT

Figure 3:
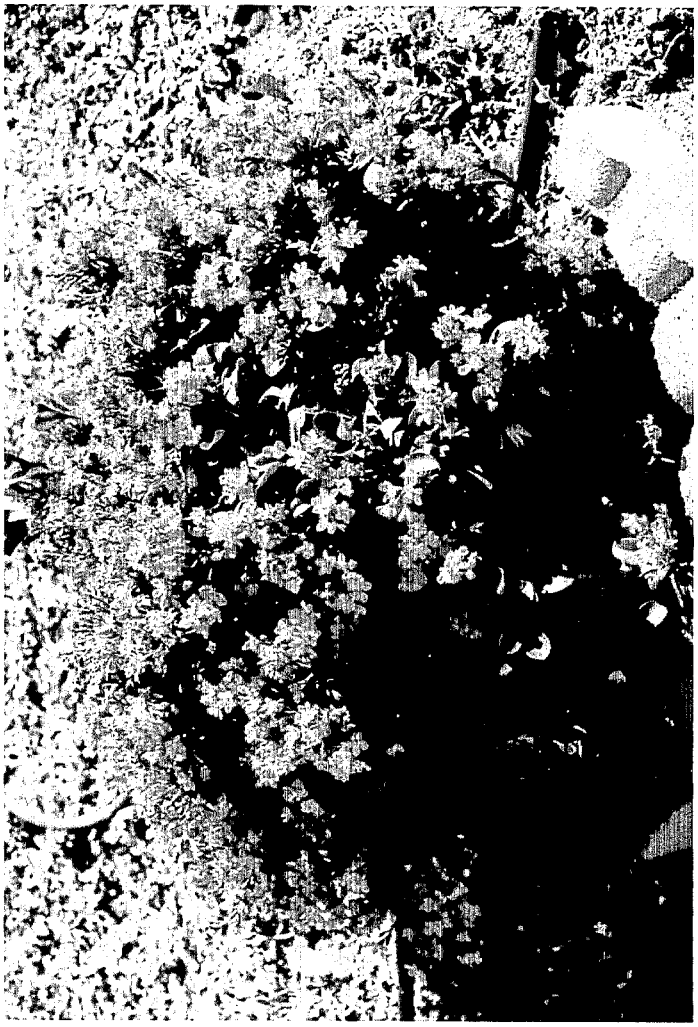
FIG. 3 shows an unpruned field-grown specimen demonstrating the very tight, compact habit of the new cultivar.

The ultimate height of this new Rephiolepis selection is unknown, as no specimen has yet reached full maturity. Present indications are that the height will range between 60 and 90 cm (2 and 3 ft). The growth habit is tight and compact (FIG. 3) and the growth rate is slow in nature.

Foliage:

*Arrangement.*—Alternate.

Figure 4:
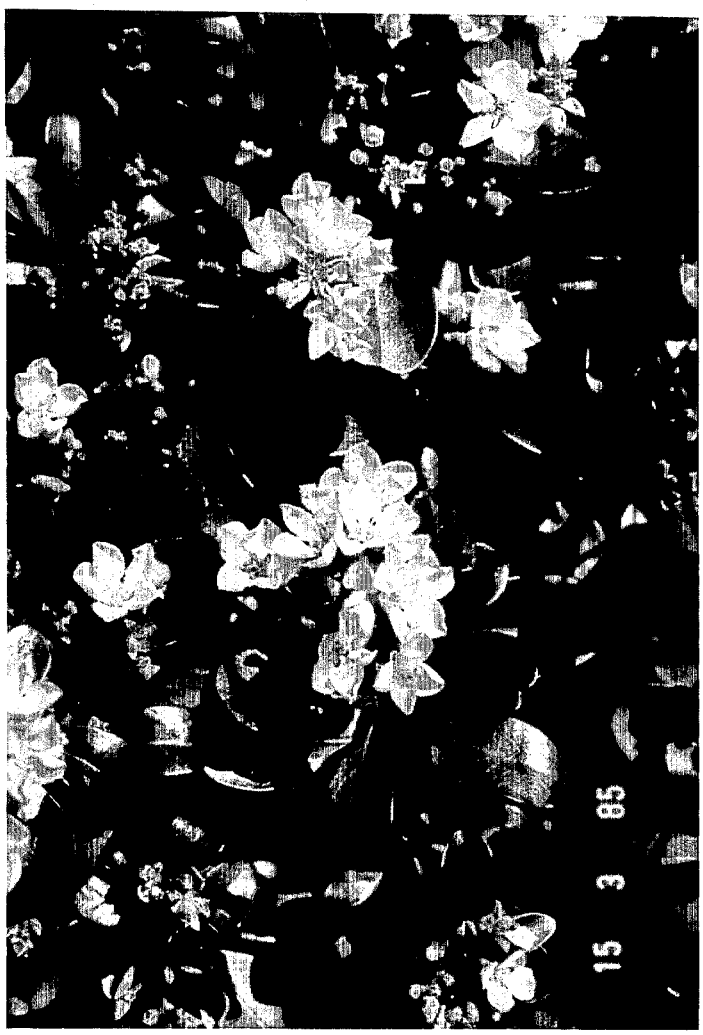
FIG. 4 is a close-up photograph showing the color of past prime flowers, which still retain their cupped form, and also showing the glossy, dark green foliage.

*Size.*—45 to 75 mm (1¾ to 3 in) in length and 20 to 25 mm (¾ to 1 in in width. '*Color.*—Upper surface: R.H.S. Colour Chart Fan 3, Yellow-Green Group No. 147A (FIG. 4). Lower surface: Fan 3, Yellow-Green Group No. 146C with veins in Fan 3, Yellow-Green Group No. 146A.

*Shape.*—Elliptic to obovate with obtuse tips.

*Margins.*—Entire.

*Texture.*—Coriaceous.

*Juvenile foliage.*—Pubescent, velutinous.

*Petioles.*—0 to 6 mm (0 to ¼ in).

Inflorescence:

Flowers are in panicles of racemes 60 to 75 mm (2½ to 3 in) in length.

*Bloom period.*—Late winter through spring months.

Figure 1:
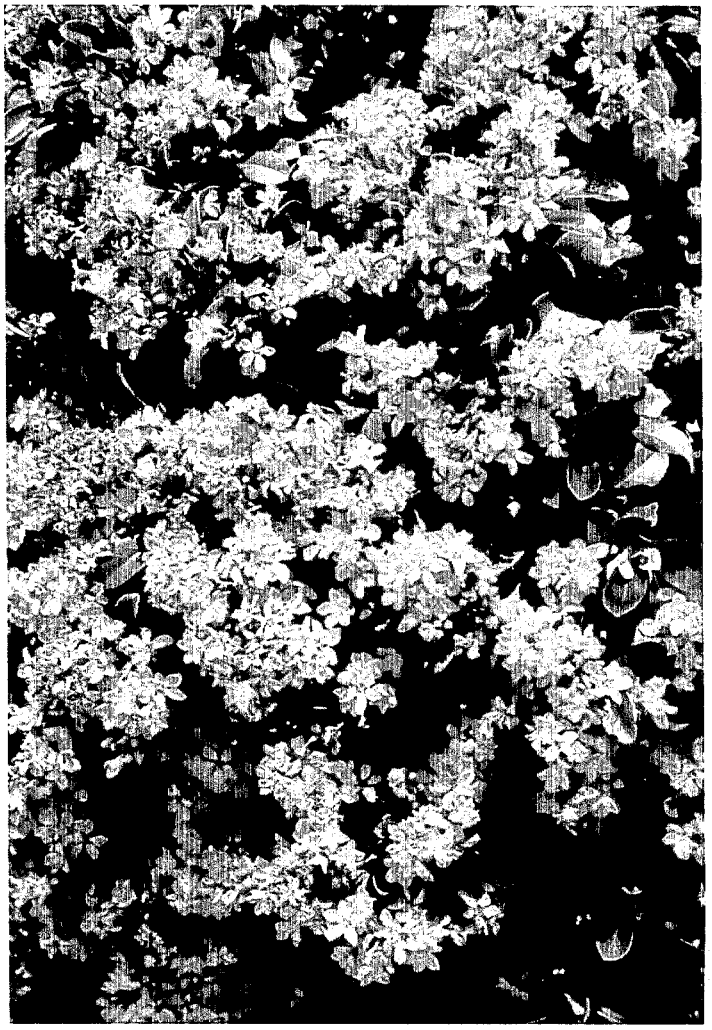

*Flower color.*—Royal Horticultural Society Colour Chart, Fan 2, Red-Purple Group No. 57B (FIG. 1), fading with age to Fan 2, Red-Purple Group No. 61D (FIG. 4). The center is Light-Pink, Fan 2, Red-Purple Group No. 62D, but it is not conspicuous as the petals do not open fully. Flower color fades with age to Red-Purple Group 61D.

*Flower diameter.*—14 mm (9/16 in) as measured by a micrometer.

*Petal shape.*—Obovate with emarginate tip. Petals emerge convolute and remain cupped when fully open.

*Petal number.*—5, seldom 6.

*Peduncle.*—0 to 6 mm (0 to ¼ in) in length.

*Fruit.*—Drupelike pome. Color: R.H.S. Colour Chart, Fan 4, Black Group No. 202A.

DESCRIPTIONS OF OTHER POTENTIALLY SIMILAR RAPHIOLEPIS CULTIVARS

Figure 2:
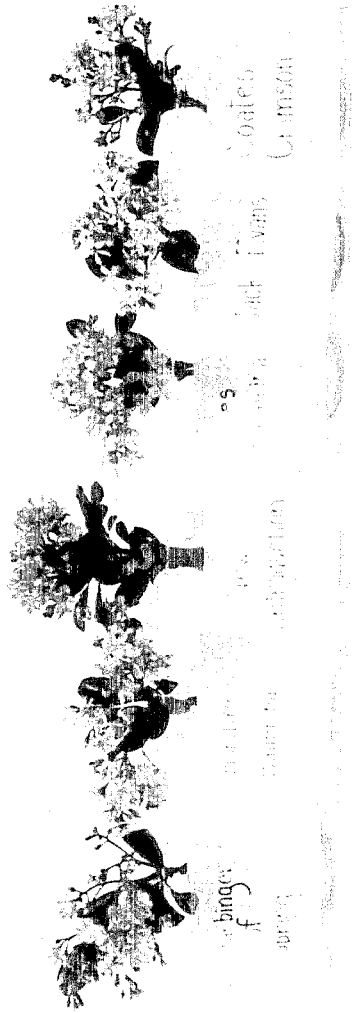

Descriptions and comparisons are based on an average of not less than 20 specimens for each specified characteristic (FIG. 2). Comparisons were formulated from side-by-side evaluations of both container and field-grown specimens of each of the cultivars listed below. These cultivars were chosen on the basis that they represent the most similar cultivars that have ever been offered in the nursery trade. Comparison plants are all the same age and have been grown in the same environment and with the exact same cultural techniques.

*Raphiolepis indica* 'Ballerina'

Flower color: Deep Rosy-Pink, Red-Purple Group 67D, similar to but definitely not as dark as the new selection.
Plant habit: Compact.
Plant height: 90 to 120 cm (3 to 4 ft).
Leaf width: 62 mm (2½ in).
Leaf margins: Entire and sinuate.

*Raphiolepis indica* 'Coates Crimson'

Flower color: Crimson-Pink flowers, Red-Purple Group 58C; not as dark as the new Raphiolepis selection.
Plant habit: Compact, spreading.
Plant height: 60 to 120 cm (2 to 4 ft).
Leaf length: 54 mm (2 in).
Leaf width: 22 mm (¾ in).
Leaf margins: Entire.

*Raphiolepis indica* 'Spring Rapture'

Flower color: Rose-Red blooms, Red-Purple Group 61D.
Plant habit: Compact, mounding.
Plant height: 60 to 120 cm (2 to 4 ft).
Leaf length: 61 mm (2½ in).
Leaf width: 24 mm (1 in).
Leaf margins: Serrate.

*Raphiolepis indica* 'Ballerina'

Flower color: Bronzy-Green, rich pink flowers. Flower color Red-Purple Group 68A.
Plant habit: Graceful habit.
Plant height: 120 to 180 cm (4 to 6 ft).
Leaf length: 82 cm (3½ in).
Leaf width: 37 cm (1¼ in).
Leaf margins: Serrate.

I claim:

1. A new and distinct variety of *Raphiolepis indica,* substantially as herein shown and described, characterized as to novelty by:
   flower petals having a unique, dark, rich vivid red-purple color;
   flowers that remain somewhat cupped, never fully expanding; and
   a slow growing nature and tight, compact habit.

* * * * *